US006262041B1

(12) United States Patent
Serbinova

(10) Patent No.: US 6,262,041 B1
(45) Date of Patent: *Jul. 17, 2001

(54) USE OF VITAMIN D ANALOGS TO TREAT CONDITIONS RELATED TO INCREASED OXIDATIVE STRESS

(75) Inventor: Elena Serbinova, El Sobrante, CA (US)

(73) Assignee: Bertek Pharmaceuticals, Inc., Foster City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/287,544

(22) Filed: Apr. 6, 1999

Related U.S. Application Data

(60) Provisional application No. 60/080,913, filed on Apr. 6, 1998.

(51) Int. Cl.[7] .......... A61K 31/59

(52) U.S. Cl. .......... 514/167

(58) Field of Search .......... 514/167

(56) References Cited

U.S. PATENT DOCUMENTS

| | | | |
|---|---|---|---|
| 5,098,899 * | 3/1992 | Gilbert et al. | 514/167 |
| 5,747,479 | 5/1998 | Bryce et al. | 514/167 |
| 5,804,574 | 9/1998 | Bryce et al. | 514/167 |

OTHER PUBLICATIONS

SCRIP World Pharmaceutical News No. 2241, p. 26, Jun. 17, 97.

* cited by examiner

*Primary Examiner*—Jerome D. Goldberg
(74) *Attorney, Agent, or Firm*—Cooley Godward LLP

(57) ABSTRACT

A pharmaceutical composition for reducing the rate at which skin ages or for treating cancer, acne or rosacea. The composition comprises a pharmaceutically acceptable excipient in combination with 26, 27-hexafluoro-1,25-dihydroxy vitamin $D_3$. The composition is preferably administered topically at a concentration of about 0.0001% weight to about 0.01% weight.

3 Claims, No Drawings

USE OF VITAMIN D ANALOGS TO TREAT CONDITIONS RELATED TO INCREASED OXIDATIVE STRESS

CROSS-REFERENCE

This application is a continuation-in-part of provisional application 60/080,913 filed Apr. 6, 1998.

ACKNOWLEDGEMENTS

This invention was supported in part by grants from the Small Business Research Program through the National Institutes of Health (National Institute of Aging) Grant #1R43AG13572/01A. The U.S. Government may have rights in this invention.

INTRODUCTION

1. Technical Field

This invention relates to the treatment of conditions related to increased oxidative stress and/or antioxidant depletion on epithelial cells by the administration of vitamin D analogs to a human. Thus, a vitamin D analog is used to treat cancer, rosacea and acne and to reduce the rate at which skin ages.

2. Background

The involvement of free radicals and reactive oxygen species in environmental stress conditions such as hyperoxia, hypoxia, reperfusion, heat shock, and metabolism of environmental pollutants and toxic chemicals is well documented. Experimental and clinical evidence also increasingly implicates free radicals in various pathological conditions in skin, such as ionizing irradiation damage, thermal trauma, phototoxic injury, photo allergy, and drug toxicity. This can lead to accelerated aging of the skin, acne, rosacea and/or cancer of the skin. It is known that certain antioxidant defense systems serve to protect skin against free radical-induced damage. It has been noted that individuals with skin types I and II have the yellow-red pigment pheomelanin, which is highly photoreactive and capable of sensitizing free radical production.

Skin antioxidant systems have a finite capacity to reduce oxidative stress or prevent the depletion of natural antioxidants. If oxidative stress persists, the skin's endogenous reserves may be exceeded, and free radical concentrations will increase, leading to cellular damage, such as lipid peroxidation, formation of modified bases in DNA, and DNA strand breaks. Production of hydroxyl- or peroxyl radicals and other activated oxygen species, implicated in the initiation of lipid peroxidation as well as the amount of lipid peroxidation products, such as malondiadlehyde, lipid hydroperoxides, and lipids with conjugated dienes, can be used as markers of cellular damage to indicate the level of damage from oxidative stress.

Increased oxidative stress and antioxidant depletion result in accelerated skin aging which is manifested with skin wrinkling, thickening and sagging, and increased number of senile lentigines (liver spots). Persons with damaged skin and keratinization disorders are at high risk for malignant lesions such as basal and squamous cells carcinoma.

Vitamin D3 is formed in humans by the action of sunlight on skin, and thus its antioxidant action should help protect the cells in which it is formed against the aging and carcinogenic effects of ultraviolet light caused in part by peroxidation of cell membranes.

Vitamin $D_3$ has the following formula and numbering system:

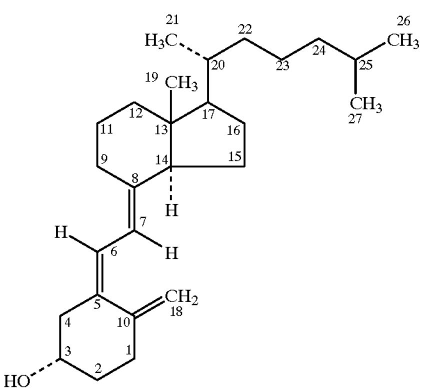

We have found that the administration of 26,27-hexafluoro-1,25-dihydroxy-vitamin $D_3$ (also referred to as ST-630) to humans is useful for reducing the rate at which skin ages and for treating acne, rosacea and cancer.

SUMMARY OF THE INVENTION

One aspect of this invention is a pharmaceutical composition for reducing the rate at which skin ages, and for treating acne, rosacea and epithelial cancer, which composition comprises a pharmaceutically-acceptable excipient in combination with ST-630.

Another aspect of this invention is a process for treating acne or rosacea in the skin in a human, which process comprises administering ST-630 to a human in need thereof on a daily basis in an amount sufficient to reduce the severity of the acne or rosacea.

Another aspect of this invention is a process for reducing the rate at which skin of a human ages, which process comprises topically administering ST 630 to the skin of the human on a daily basis in an antioxidative amount for a time sufficient to reduce the rate of skin aging.

Another aspect of this invention is a process for treating epithelial cancer. The process comprises topically administering ST-630 to the epithelial cancer on a daily basis for a time sufficient to alleviate the cancer.

Another aspect of this invention is an article of manufacture that comprises a topical pharmaceutical composition as described in combination with written instructions for performing the process of reducing the rate of skin aging or treating skin cancer, acne or rosacea.

Another aspect is a process for preparing a topically-applied pharmaceutical composition, which process comprises combining ST-630 with a pharmaceutically-acceptable excipient to form a topically-applied composition useful for reducing the rate at which skin ages and for treating acne, rosacea and epithelial cancer.

DESCRIPTION OF SPECIFIC EMBODIMENTS

The compound useful in this invention has the following formula:

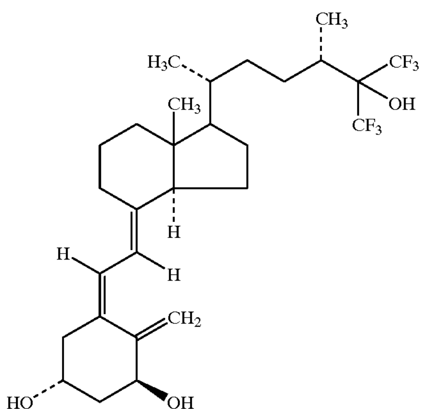

The name of the compound is 26,27-hexaflouro-1,25-dihydroxy-vitamin $D_3$, also known as ST-630. The compound is described in U.S. Pat. No. 4,358,406 to De Luca et al, which is incorporated herein by reference. The compound may be purchased from Tetrionics, 565 Science Dr., Madison, Wis. 53711. It may also be purchased from Sumitomo Pharmaceuticals Co., 2-3 Doshomachi 2 Chome, Chrio-Ku, Osaka, 541, Japan. The compound will be referred to in this application as ST-630.

A first aspect of this invention is a pharmaceutical composition for administration to a human comprising a combination of a pharmaceutically acceptable excipient and ST-630. The amount of ST-630 present will be determined by the use of the composition. For treating acne in a human, an amount sufficient to decrease the intensity of the condition will be used. For reducing the rate of skin aging, an amount that has an antioxidative effect will be used. For treatment of cancer, an amount having an anticarcinogenic effect is administered. For treating rosacea, an anti-inflammatory amount will be used. Generally, the amount of ST-630 in the composition of this invention will vary from about 0.1 micrograms/gram to about 100 micrograms/gram. The composition may be in a form that is suitable for oral or topical administration, preferably topical. The amount administered over time is discussed hereinafter.

Preferably, the composition is in a form to be administered topically, thus, the composition may be a solution, emulsion (i.e. an ointment, cream or lotion), suspension, gel, or other composition which is applied topically. The pharmaceutical excipients that are useful may be water soluble or water insoluble depending on the desired final product. The dosage form which is prepared in accordance with this invention may be prepared by dissolving the active ingredient in a solvent that is miscible or nonmiscible in water, by suspending the agent in an appropriate medium, or by incorporating the agent into one of the two phases of an oil and water system. In general, it is preferred to prepare a composition which is an emulsion, that is a two-phase system prepared by combining two emulsible liquids, one of which is dispersed uniformly throughout the other. The topically-applied composition is preferably an ointment, i.e., semisolid preparations intended for external application to the skin or mucous membranes.

An ointment encompaases petroleum, i.e., oleaginous bases, emulsion bases—either water-in-oil (W/O) or oil-in-water (O/W)—and the so-called water-soluble bases. Oleaginous bases are described as ointments, but emulsion bases may be termed creams or lotions. The ointment base should be nonirritating, easily removable, nonstaining, stable, non-pH-dependent and compatible with ST-630.

Generally the ointment composition of this invention may be categorized as follows:

Hydrocarbon Bases (Oleaginous)

Example: White Petroleum, White Ointment

1. Emollient
2. Occlusive
3. Nonwater-washable
4. Hydrophobic
5. Greasy

Absorption Bases (Anhydrous)

Examples: Hydrophilic Petrolatum; Anhydrous Lanolin

1. Emollient
2. Occlusive
3. Absorb Water
4. Anyhydrous
5. Greasy

Absorption Bases (W/O [water in oil] Type)

Examples: Lanolin, Cold Cream

1. Emollient
2. Occlusive
3. Contain Water
4. Some absorb additional water
5. Greasy Water-Removable Bases (O/W Type)

Example: Hydrophilic Ointment

1. Water-washable
2. Nongreasy
3. Can be diluted with water
4. Nonocclusive

Water-Soluble Bases

Example: Polyethylene Glycol Ointment

1. Usually anhydrous
2. Water-soluble and washable
3. Nongreasy
4. Nonocclusive
5. Lipid-free A hydrocarbon base is usually petrolatum per se or petrolatum modified by waxes or liquid petrolatum to change viscosity characteristics. Liquid petrolatum gelled by the addition of a polyethylene resin is a useful hydrocarbon ointment base. Hydrocarbon ointment bases are classified as oleaginous bases. A gelled mineral oil vehicle is also useful.

Absorption bases are hydrophilic, anhydrous materials or hydrous bases that have the ability to absorb additional water. The former are anhydrous bases which absorb water to become W/O emulsions; the latter are W/O emulsions which have the ability to absorb additional water.

Hydrophilic Petrolatum USP is an anhydrous absorption base. The W/O emulsifying property is conferred by the inclusion of cholesterol. This composition is a modification of an original formulation which contained anhydrous lanolin. Inclusion of stearyl alcohol and wax add to the physical characteristics, particularly firmness and heat stability.

Commercially available absorption bases include Aquaphor (Beiersdorf) and Polysorb (Fougera). Nivea Cream (Beiersdorf) is a hydrated emollient base.

Water-washable bases or emulsion bases, commonly referred to as creams, are also useful of ointment base. Emulsion bases are washable and removed easily from skin or clothing. The emulsion base can be subdivided into three component parts, designated as the oil phase, the emulsifier and the aqueous phase. The ST-630 is included in the oil phase. The oil phase, sometimes called the internal phase, is typically made up of petrolatum and/or liquid petrolatum together with one or more of the higher-molecular-weight alcohols, such as cetyl or stearyl alcohol.

The aqueous phase of the emulsion base generally exceeds the oil phase in volume. The aqueous phase contains the preservative materials, the emulsifier or a part of the emulsifier system and humectant. The last is usually glycerin, propylene glycol or a polyethylene glycol. The humectant normally is included to minimize water loss in the finished composition.

The aqueous phase contains the preservative(s) which are included to control microbial growth. Preservatives in emulsion bases usually include one or more of the following: methylparaben and propylparaben, benzyl alcohol, sorbic acid or quaternary ammonium compounds. Propylene glycol insufficient concentration also can function as a preservative.

The aqueous phase also contains the water-soluble components of the emulsion system, together with any additional stabilizers, antioxidents, buffers, etc., that may be necessary for stability, pH control or other considerations associated with aqueous systems.

The emulsifier or emulsifier system in the cream formulation is a major consideration. The emulsifier may be anionic, nonionic or amphoteric.

Anionic Emulsifiers—Sodium lauryl sulfate, the emulsifier in Hydrophilic Ointment USP (Example 7), is typical of this class. The active portion of the emulsifiers include soaps such as triethanolamine stearate. Soaps, of course, are alkaline and, hence, incompatible with acids.

Nonionic Emulsifiers—Nonionic emulsifiers show no tendency to ionize in solution. This advantage results in excellent pH and electrolyte compatibility in such emulsions. Nonionic emulsifiers range from lipophilic to hydrophilic and hydrophilic member to produce a so-called hydrophilic-lipophilic balance (or HLB).

Many nonionic surfactants are the result of condensation of ethylene oxide groups with a long chain hydrophobic compound. The hydrophilic characteristics of the condensation product are controlled by the number of (usually) oxyethylene groups (—$OCH_2CH_2$—). Examples of nonionic surfactants are given in Table 4.

TABLE 1

NONIONIC EMULSIFIERS

| Type | Examples |
|---|---|
| Polyoxyethylene fatty alcohol ethers | Polyoxyethylene lauryl alcohol |
| Polyoxypropylene fatty alcohol ethers | Propoxylated oleyl alcohol |
| Polyoxyethylene fatty acid esters | Polyoxyethylene stearate |
| Polyoxyethylene sorbitan fatty acid esters | Polyoxyethylene sorbitan monostearate |
| Sorbitan fatty acid esters | Sorbitan monostearate |
| Polyoxyethylene glycol fatty acid esters | Polyoxyethylene glycol monostearate |
| Polyol fatty acid esters | Glyceryl monostearate<br>Propylene glycol monostearate |
| Ethyoxylated lanolin derivatives | Ethyoxylated lanolins<br>Ethoxylated cholesterol |

Emulsions containing nonionic emulsifiers usually are prepared by dissolving or dispersing the lipophilic component in the oil phase and the hydrophilic component in the aqueous phase. The two phases then are heated separately and combined as described on page 1509. The nonionic emulsifier content of an emulsion may total as much as 10% of the total weight or volume. Emulsions based on nonionic emulsifiers are generally low in irritation potential, stable and have excellent compatibility characteristics.

Water soluble ointment bases are made up of soluble components, or may include gelled aqueous solutions. The latter often are referred to as gels. Major components, and in some instances the only components, of water-soluble bases are the polyethylene glycols. These are liquids or waxy solids identified by numbers which are an approximate indication of molecular weight. Polyethylene glycol 400 is a liquid superficially similar to propylene glycol, while polyethylene glycol 4000 is a waxy solid.

Polyethylene glycols have the general chemical formula:

$$HOCH_2(CH_2OCH_2)_nCH_2OH$$

They are nonvolatile, water-soluble or water-miscible compounds and chemically inert, varying in molecular weight from several hundred to several thousands. Patch tests have shown that these compounds are innocuous and continuous use has confirmed their lack of irritation.

Polyethylene glycols of interest as vehicles include the 1500, 1600, 4000 and 6000 products, ranging from soft, waxy solids (polyethylene glycol 1500 is similar to petrolatum) to hard waxes. Polyethylene glycol 6000 is hard wax-like material melting at 58 to 62°; it is nonhygroscopic. Polyethylene glycols, particularly 1500, can be used as a vehicle per se; however, better results often are obtained by using blends of high- and low-molecular-weight glycols, as in Polyethylene Glycol Ointment NF.

Gelling agents used in these preparations may be nonionic or anionic. Nonionics include cellulose derivatives, such as methylcellulose or hydroxypropyl methylcellulose. These derivatives form gels when dissolved in water but also exhibit the characteristic of reverse solubility. The celluloses are wetted, i.e., dispersed in hot water, and then cooled to effect solution. Sodium carboxymethylcellulose is an ionic form of cellulose gelling agent. It is conventionally soluble, and not heat-insoluble.

Carbomers are the USP designation for various polymeric acids which are dispersible but insoluble in water. When the acid dispersion is neutralized with a base a clear, stable gel is formed. Carbomer 934P is physiologically inert and is not a primary irritant or sensitizer. Other carbomers for which monographcs appear in the USP include carbomers 910, 940, 941 and 1342.

Another gelling agent is colloidal magnesium aluminum silicate (Veegum). It is an inorganic emulsifier and suspending agent, as well as a gelling agent. Veegum dispersions are compatible with alcohols (20 to 30%), acetone and glycols. It frequently is employed as a gel stabilizer, rather than as the sole gelling agent.

Sodium alginate and the propylene glycol ester of alginic acid (Kelcoloid) also are satisfactorily between pH 4.5 and 10; addition of calcium ions will gel fluid solutions of sodium alginate.

Such ointments and gels can be prepared in accordance with the process and equipment set forth in Remington: The Science and Practice of Pharmacy, $19^{th}$ Edition, Volume 2, Chapter 90.

The compositions of this invention may also be prepared to be orally ingested. Such compositions include solid or liquid formulations. Solid formulations include powders, tablets, capsules (including both soft and hard gelatin capsules), and the like. Liquid formulations include solutions, suspensions, syrups, elixirs, and the like.

Generally, the composition, whether administered orally or topically will contain about 0.1 microgram (mcg) active/gram (g) of final composition to about 100 mcg/g., i.e. about 0.00001 to about 0.01% by weight.

Preferably, the topical composition of this invention will include a pharmaceutically acceptable excipient to aid in improving the cosmetic, adherence, and absorption properties of the composition. Polyurethane compounds that provide such useful properties include any conventional polyurethane compound formed by reaction of a diisocyanate with a compound having an active hydrogen, for example as disclosed in U.S. Pat. No. 4,079,028 to Emmons, which is incorporated herein by reference. A compound having an active hydrogen includes alcohols, diols, triols, amines, hydroxy-terminated polyesters, silanols, carboxylic acids, and the like. More particularly, the polyurethane compound includes compounds having the formula:

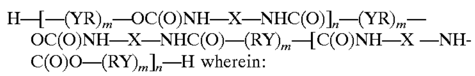

$$H—[—(YR)_m—OC(O)NH—X—NHC(O)]_n—(YR)_m—OC(O)NH—X—NHC(O)—(RY)_m—[C(O)NH—X—NH\text{-}C(O)O—(RY)_m]_{n'}—H$$ wherein:

- X is an alkylene or alkenylene radical containing from 1 to about 20 carbon atoms, or a cycloalkylene or cycloalkenylene radical containing from about 5 to 20 carbon atoms, or a mononuclear or fused ring arylene radical containing from about 6 to about 10 carbon atoms, unsubstituted or substituted with one or more lower alkyl, lower alkoxy, lower alkoxy-substituted lower alkyl, nitro or amino groups or halogen atoms;
- Y is oxygen, sulfur, silicon, or —NH—;
- each R is the same or different, and is chosen from alkylene, alkenylene, —SiR2R3—, and —CR2R3—NR4-CR2R3—, wherein R2, R3 and R4 are independently hydrogen or lower alkyl;
- m is an integer selected to provide a (YR) moiety having a molecular weight of from about 40 to about 6,000; and
- n and n' are the same or a different integer from 0–30 inclusive, correlated with m so as to provide a polyurethane compound having a molecular weight of up to about 200,000.

Polyurethane compounds where YR is $—SiR_2R_3—$or $—CR_2R_3—NR_4—CR_2R_3—$are well known in the art (See for example U.S. Pat. No. 5,286,787 to Padolo and Majolo; U.S. Pat. No. 4,962,178 to Harisiades; U.S. Pat. No. 4,155,892 to Emmons, et. al., and "Polyurethanes Chemistry and Technology" by J. H. Saunders and K. C. Frisch, Interscience Publishers, pp. 65–67.) Preferred are polyurethanes that are hydroxy-terminated polyurethanes, i.e. where Y is oxygen, especially those where R is alkylene or alkenylene, which are disclosed in U.S. Pat. Nos. 4,971,800, 5,045,317, and 5,051,260, the complete disclosures of which are hereby incorporated by reference. Also useful are those disclosed in U.S. Pat. No. 4,079,028 issued Mar. 1978, to Emmons, et al. This, too, is incorporated herein by reference.

A preferred hydroxy-terminated polyurethane has the above formula where X is 4,4'-dicyclohexylmethane, Y is oxygen, R is 1,2-propylene, m is 1–4, n and n' are both 12. It has a tradename of Polyolprepolymer-2, and is prepared by the reaction of 2 moles of polypropylene glycol and 1 mole of dicyclohexylmethane diisocyanate in the presence of stannous octoate, as detailed in U.S. Pat. No. 4,971,800, Examples 1 and 5. It has a CAS# 9042-82-4, and a CAS name poly[oxy(methyl-1,2-ethanediyl)], α-hydro-ω-hydroxy-, polymer with 1,1 '-methylene-bis-[4 -isocyanatocyclohexane]. Also preferred is Polyolprepolymer-14, which has the same CAS# and name, but a higher molecular weight (a weight average molecular weight of 14,000 as opposed to 4,000 for Polyolprepolymer-2), and Polyolprepolymer-1 5, which has a CAS# 39444-87-6, and is named poly(oxy-1,2-ethanediyl), ochydro-o)-hydroxy-, polymer with 1,1'-methylene-bis-[4-isocyanatocyclohexane]. Generally, the optional adhesion-promoting agent will be present in an amount of 0% wt. to about 15 wt., preferably about 0.5% wt. to about 10% wt., and more preferably about 0.5 % wt. to about 5% wt.

Treatment of Acne

Acne is a common inflammatory pilosebaceious disease characterized by comedones, papules, pustules, inflamed nodules, superficial pus-filled cysts, and (in extreme cases) canalizing and deep, inflamed, sometimes purulent sacs. The pathogenesis is complex. An interaction between hormones, keratinization, sebum, and bacteria somehow determines the course and severity of acne. It begins at puberty, when the increase in androgens causes an increase in the size and activity of the pilosebaceous glands. The earliest microscopic change is thought to be intrafollicular hyperkeratosis, which leads to blockage of the pilosebaceious follicle with consequent formation of the comedo, composed of sebum, keratin, and microorganisms, particularly *Propionibacterium acnes.* Lipases from *P. acnes* break down triglycerides in the sebum to form free fatty acids (FFA), which irritate the follicular wall. Retention of sebaceous secretions and dilation of the follicle may lead to cyst formation. Rupture of the follicle, with release of FFA, bacterial products, and keratin constituents into the tissues, induces an inflammatory reaction that usually results in an abscess that heals with scars in severe cases.

For therapy and prognosis, acne is best classified as superficial or deep according to the severity of the predominating lesions.

Superficial acne is characterized by comedones, either open (blackheads) or closed (whiteheads); inflamed papules; superficial cysts; and pustules. Large cysts occur occasionally, sometimes after manipulation or trauma to an otherwise uninflamed blackhead. In deep acne, deep inflamed nodules and pus-filled cysts, which often rupture and become abscesses, are also present; some of them open on the skin surface and discharge their contents. Scarring is frequent. Lesions are most common on the face, but the neck, chest, upper back, and shoulders may also be affected.

The anti-acne effect of the composition of this invention is based on the observation that ST-630 has an antibacterial effect versus P. acnes, ST-630 stimulates oxidative burst in neutrophils, and ST-630 protects keratinocytes against oxidative stress in phospholipids and against apoptosis.

In treating acne in accordance with the method of this invention ST-630 is topically applied to the acne-infected area and retained there in an amount sufficient to effect the reduction in the severity of the acne. Generally the composition is applied for a period of time, e.g. up to 24 hours, preferably no more than about 12 hours, then removed by washing. This process is continued until the acne is significantly reduced. Generally, no more than a few nanograms will be applied to about a square centimeter of the acne-infected area of skin. The amount will be consistent with the concentration in the composition.

Treatment of Rosacea

Rosacea is a chronic inflammatory disorder, usually beginning in middle age or later, and characterized by telangiectasia, erythema, papules, and pustules appearing especially in the central areas of the face. Tissue hypertrophy, particularly of the nose (rhinophyma), may result. Occasionaslly, rosacea occurs on the trunk and extremities.

The cause is unknown, but the disease is most common in persons with a fair complexion. Diet probably plays no role in the pathogenesis. Rosacea may resemble acne, but comedones are never present; differential diagnosis also includes drug eruptions (particularly from iodides and bromides), granulomas of the skin, cutaneous LE, and perioral dermatitis.

Treatment is essentially the same as acne. The anti-rosacea effect is based on the effect versus *P. acnes*, the stimulation of oxidative burst in neutrophils, and the protection of heretinocytes against oxidative stress in phospholipids and against apoptisis.

Treatment of Aging Skin

The effect of the composition of this invention on the reduction of the rate at which skin ages is based, i.e., on the protective effects of ST-630 on the skin of nude mice against oxidative stress induced by UV(A+B)-irradiation, the anti-proliferative and prodifferentive activities of ST-630, and the penetration of ST-630 through the skin.

In reducing the rate of aging of the skin, the composition of this invention is applied on a regular basis to human skin. Premature aging of the skin is brought on by factors that may relate to the genetics of the person or the environment in which the person is located. In general, the topical composition is simply rubbed onto the skin and kept on for a period of time such as for about one to twelve hours a day or even up to 24 hours. The composition is generally washed off after it has been on and a new composition put on.

Treatment of Cancer

Skin cancers (e.g., basal cell and squamous cell carcinomas), the most common malignancies, arise in sun-exposed areas of skin. The incidence is highest in outdoor workers, sportsmen, and sunbathers and is related to the amount of melanin skin pigmentation; light-skinned persons are most susceptible. Such neoplasms may also develop years after x-ray or radium burns or arsenic ingestion.

Less common malignancies include malignant melanoma, Paget's disease of the nipple or extramammary Paget's (usually near the anus), Kaposi's sarcoma, and cutaneous T cell lymphoma.

The clinical presentation and biologic behavior of basal cell carcinomas are highly variable. They may appear as small, shiny, firm, almost translucent nodules; ulcerated, crusted lesions; flat, scar-like indurated plaques; or lesions difficult to differentiate from psoriasis or localized dermatitis. Most commonly the carcinoma begins as a small shiny papule, enlarges slowly, and, after a few months, shows a shiny, pearly border with prominent engorged vessels (telangiectases) on the surface, and a central dell or ulcer. Recurrent crusting or bleeding is not unusual, and the lesion continues to enlarge slowly. It is common for basal cell carcinomas to alternately crust and heal, which may decrease the concern of both patient and doctor about the important of the lesion. Basal cell carcinomas rarely metastasize but may be very destructive by invading normal tissues. Rarely, death may ensue because the basal cell carcinoma invades or impinges on underlying vital structures or orifices (eyes, ears, mouth, bone, dura mater). Because of the highly variable appearance of basal cell carcinomas, the differential diagnosis is extensive.

Squamous cell carcinomas arise from the malpighian cells of the epithelium. Most appear on sun-exposed areas, but they may occur anywhere on the body. A squamous cell carcinoma may develop in normal tissue, in a preexisting actinic keratosis or patch of leukoplakia, or in burn scars. The clinical appearance of squamous cell carcinomas is highly variable. The tumor begins as a red papule or plaque with a scaly or crusted surface. It may then become nodular, sometimes with a warty surface. In some, the bulk of the lesion may lie below the level of the surrounding skin. Eventually it ulcerates and invades the underlying tissue. The percentage of squamous cell carcinomas of the skin that metastasize is unknown but is probably quite low. About ⅓ of lingual or mucosal lesions have metastasized before they have been diagnosed. Differential diagnosis includes many types of benign and malignant lesions including basal cell carcinoma, keratoacanthoma, actinic keratosis, and seborrheic keratosis.

Bowenoid papulosis—human papillomavirus-induced lesions that occur as single or, more often, as multiple lesions on the genitalia—are distinct from Bowen's disease.

A malignant melanocytic tumor arising in a pigmented area: skin, mucous membranes, eyes, and CNS. Malignant melanomas vary in size, shape, and color (usually pigmented), and in their propensity to invade and metastasize. Thus, this neoplasm may spread so rapidly that it will be fatal within months of its recognition, while the 5-year cure rate of early, very superficial lesions is nearly 100%. Early suspicion by inspection and an adequate biopsy for histologic determination of tumor thickness are the only means of effective management and an optimum prognosis.

Most malignant melanomas arise from melanocytes in normal skin; about 40 to 50% develop from pigmented moles. The following danger signals suggest malignant transformation of pigmented nevi: change in size, change in color, especially spread of red, white, and blue pigmentation to surrounding normal skin; change in surface characteristics, consistency, or shape; and especially signs of inflammation in surrounding skin. Although melanomas are more common during pregnancy, pregnancy does not increase the likelihood that a mole will become a melanoma. Malignant melanomas are very rare in children but car arise from large pigmented moles (giant congenital nevi) that are present at birth.

Types, Symptoms, and Signs of Cancers

Four major types of melanoma are described. The prognosis of each type depends largely upon the histologically determined thickness of the melanoma.

1. Lentigo-maligna melanoma arises from lentigo maligna (Hutchison's freckle or malignant melanoma-in-situ); it appears on the face or other sun-exposed areas in elderly patients as an asymptomatic, large (2 to 6 cm), flat, tan or brown macule with darker brown or black spots scattered irregularly on its surface. In lentigo maligna, both normal and malignant melanocytes are confined to the epidermis; in lentigo-malignant melanoma, the malignant melanocytes invade the dermis. After variable periods, about ⅓ of the lentigo malignas develop a progressive malignant focus when cells invade the dermis; therefore, early excision—before the lesion is very large—is recommended. Most other treatment methods usually do not reach deep enough into the involved follicles, which must be removed.

2. Superficial spreading melanoma accounts for ⅔ of all melanomas. Usually asymptomatic, it is initially much smaller than the lentigo-maligna melanoma and occurs most commonly on women's legs and men's torsos. The patient seeks help after noting enlargement or irregular coloration: The lesion is usually a plaque with raised, indurated edges, and often shows red, white and blue spots or small, sometimes protuberant, blue-black nodules. Small surface indentations may be noted. Histologically, atypcial melanocytes characteristically invade both dermis and epidermis.

3. Nodular melanoma constitutes 10 to 15% of all melanomas. It may occur anywhere on the body and is seen as dark, protuberant papules or a plaque that varies in color from pearl to gray to black. Unless it ulcerates, nodular melanoma is asymptomatic, but the patient usually seeks advice because the lesion enlarges rapidly, often with little radial growth. Occasionally, a lesion contains little if any pigment.

4. Acrolentiginous melanoma is uncommon. It arises on palmar, plantar, and subungual skin and has a characteristic histologic picture similar to lentigo-maligna melanoma. It is the most common form of melanoma in Blacks.

The anticancer effect of the composition of this invention is based, i.a., on the antiproliferative and prodifferentive activities of ST-630 and its effect on the AMVN-induced hypodisploydy (apoptosis) in keratinocytes.

Another aspect of the invention is the composition of this invention in combination with written instructions for administering topically to a person in need thereof to prevent premature aging of the skin or to treat acne, rosacea or cancer.

EXAMPLES

Example 1

This example provides a method for determining the antioxidant protection of ST-630 in keratinocytes.

Keratinocytes are cells of epithelial lineage that play a major role in the structure and function of the skin. Keratinocyte function is dependent on the ligands secreted by fibroblasts in the adjacent stromal layer, whose receptors are present on the keratinocyte membrane. Such receptor-ligand reactions are primarily responsible for growth and differentiation of keratinocytes. Keratinocytes, which make up approximately 95% of the epidermal cell mass, also play a key role in initiating and modulating inflammatory processes in the skin.

Several factors contribute to the dysfunction of keratinocytes leading to the premature aging of the skin. Oxidative stress, in keratinocytes has been implicated in the damage to the skin. Oxidative stress can be induced in keratinocyte cultures in vitro by a number of different chemicals. One of the most commonly used chemicals is 2,2'-azobis-(2,4-dimethyl-valeronitrile), AMVN, a lipid-soluble azo-initiator that generates peroxyl radicals at a constant rate (at a given temperature) independently of intracellular metabolism. An interesting feature of this model system is that radical species generated in this way do not escape from the hydrophobic lipid environment. This permits the study of antioxidant properties of hydrophobic compounds.

Effect of AMVN on the phospholipid composition in keratinocytes. To determine the role of ST-630 in the pro-/anti-oxidant status of keratinocytes a sensitive assay of oxidative stress was developed that does not result in loss of viability of the cells yet was sufficiently sensitive to detect oxidative damage. Since the target site of ST-630 is believed to be confined to the cell membranes, an index of oxidative stress in membranes was required. Initial studies were undertaken to attempt to use the loss of polyunsaturated membrane phospholipids as a measure of an oxidative stress that was lower than that observed to kill the cells. Phosphatidycholine (PC) represents about half of the total phospholipid with phosphatidylethanolamine (PEA) the next most prominent phospholipid.

Comparison of the antioxidant potency of ST-630 with that of calcitriol and alpha-tocopherol in live keratinocytes using the cis-parinaric acid (PnA) assay IU. Keratinocytes were incubated in the presence of a complex of PnA with human serum albumin (PnA-HSA) for up to 2 hr to incorporate PnA into cellular phospholipids. Preliminary studies showed that the maximal incorporation of PnA into all detected phospholipid classes of keratinocytes was reached within 2 hr of incubation. The incorporation of PnA in the various phospholipids was differential and the amount of PnA incorporated was in the following order: PC>PEA>PI>PS>SPH>DPG. The constituent phospholipids were separated from the total lipid extract by HPLC. Major fluorescence peaks were identified using authentic phospholipids standards including DPG, PI, PEA, PS, PC and SPH. Control incubations of cells with has alone showed no fluorescent HPLC components, under the excitation and emission limits used.

To determine the effects of ST-630 on keratinocytes subjected to oxidative stress cell suspensions labeled with PnA were incubated with or without ST-630 (5–500 nM) in the dark at 37° C. for 1 hr in the presence of 0.5 MM AMVN. Based on the known rate constant of AMVN decomposition under the experimental conditions employed (Niki, 1990), at 0.5 mM it can be estimated that 2.4 nanomoles (nmoles) of peroxyl radicals are generated per hour at 37° C. in each incubation containing $10^6$ cells. Incubation of keratinocytes with AMVN for 1 hr induced significant oxidation of all the detected phospholipids. Trypan blue exclusion from cells after incubation showed that ST-630 at concentrations from 5 to 500 nM did not result in significant loss cell viability.

We found that all three compounds reduced the loss of all PnA-labeled phospholipid from oxidation. Concentration-dependencies of the protective effect were, however, different. ST-630 and calcitriol exerted a two-phase protection pattern. The maximum antioxidant effectiveness for calcitriol was achieved at concentrations 25–50 nM after which its antioxidant protection declined. For ST-630, the concentrations exceeding 100 nM afforded maximum and almost complete protection against AMVN-induced oxidation. Finally, vitamin E's antioxidant action was comparable to that of ST-630 at concentrations 250 and 500 nm. The data demonstrate that at this concentration the antioxidant effectiveness of ST-630 was similar to that of vitamin E and they both were much superior as antioxidants than calcitriol.

Comparison of the effects of ST-630 and calcitriol on AMVN-induced hypodiploidy (apoptosis) in keratinocytes. Nucleus/DNA of cells treated with chemical or physical agents undergo changes primarily by the activation of the nucleases, before they lose the membrane integrity. Such changes are due to the loss of DNA or fragmentation of the nucleus into apoptotic bodies. Flow cytomeric analysis of a population of cells can reveal the appearance of a hypodiploid population and changes in the stages of the cell cycle.

AMVN induces changes in the cell cycle pattern and it can be modified either by calcitriol or ST-630. (Data was collected so that the x-axis (fluorescence) of the resulting histograms could be displayed on a log scale). AMVN-derived peroxyl radicals primarily cause damage to the DNA and repair of DNA is accomplished during the G1 or G2 block. When keratinocytes were treated with various concentrations of ST-630 or calcitriol, and subsequently exposed to AMVN there was a considerable reduction in the level of hypodiploid cells. This effect was concentration-dependent. For example, calcitriol at the concentration of 10 nM blocked the cells at the G2/M phase of the cell cycle and at the same time reduced the hypodiploidy by 40%. The highest concentration of calcitriol used, i.e. 500 nM reduced the hypodiploidy by 60%. These results indicate that calcitriol can block the induction of hypodiploidy-induced by AMVN in human keratinocyte cells. The fluorinated analog, ST-630, was even more potent in blocking hypodiploidy. 10 nM of ST-630 blocked the hypodiploidy by 60%. In the range from 100 to 500 nM, ST-630 completely protected keratinocytes from the adverse effects of AMVN.

Example 2

This example provides studies of oxidative burst and chemotaxis in human neutrophils.

Oxidative (respiratory) burst in polymorphonuclear nuetrophils (PMN) is a major mechanism of defense against bacterial and/or viral pathogens. Oxidative burst is a complex process resulting in the generation by PMN of a huge amount of oxygen free radicals (superoxide and hydroxyl radicals) and chemically reactive substances—hydrogen peroxide and hypochlorite. The mechanism of cell activation involves such steps as increase of intracellular $Ca^{2+}$ concentration upon the interaction of activator, increasing the activity of protein kinase C, activation of NADPH oxidase with subsequent generation of superoxide radicals and hydrogen peroxide in the phagosomes and in the surrounding area, releasing and activation of myeloperoxidase and production of hypochlorite (HOCL).

Comparison of the effects of St-630 and calcitriol on oxidative burst in human neutrophils. The respiratory burst in PMNLs (isolated from fresh heparinized whole blood by dextran sedimentation) was initiated by the addition of N-formylmethionyl-leucyl-phenylalanine-methylester, FLPM ($10^{-7}$M), phorbol12,13-miristate, acetate, PMA (0.01 μg/ml) and opsonized zimozan (1.0 mg/ml). Superoxide production was assayed by the superoxide dismutase-inhibitable reduction of cytochrome c. FIG. 8 shows the dependence of superoxide production (included by standard stimulants as indicated) on the concentration of ST-630 or calcitriol. It appears that both compounds, but especially ST-630 act to prime for supertoxide release when cells are treated with known stimulants. The higher effectiveness of ST-630 (as compared with calcitriol) was evident in the range of concentrations from 25 to 100 nM whereas at higher concentrations the difference was no longer observed. In addition, a greater effectiveness of ST-630 to stimulate oxidative burst in PMNLs (compared to calcitriol) was achieved when opsonized zymosan or FLPM were used as stimulants. The difference was less pronounced with PMA.

Comparison of the effects of St-630 and calcitriol on chemotaxis in human neutrophils. For chemotaxis assay, chemotactic solution (medium 199 containing 0.5% BSA and FLPM) and multiwell chamber were used. The numbers of migrated neutrophils for different concentrations of FLPM (as a chemotactic factor) were within the usually observable range (see Table 4 in the Appendix). The chemotaxis data in the presence of different concentrations of ST-630 or calcitriol showed considerable variability (based on error levels which were fairly large in some cases). Despite this, the data are consistent with the effects of these compounds on superoxide release. Both ST-630 and calcitriol appear to be inhibitory when higher concentrations of FLPM were used.

Example 3

This example shows the antibacterial effect of ST-630 and calcitriol against Propionibacterium acnes.

*Propionibacterium acnes,* the target of inflammation in acne, was tested for its sensitivity to ST-630 and calcitriol using the inhibition method standardly employed for assessment of antibiotic efficiency. The strain (lyophilized) P. *acnes* (batch # 96-09SV) was received from the U.S. type culture collection (Rockville, Md.). It was revitalized in 0.5 ml freshly boiled (10 min) reinforced Clostridial medium. ST-630 or calcitriol dissolved in 5.0 μl DMSO were applied onto the top of sterilized discs made of filter paper (6 mm). Erythromycin (15 μg) and DMSO (5.0 μl) were used as controls (positive and negative, respectively). The plates were incubated for 48 hr at 36° C. and the diameter of the inhibition zone was measured. Neither DMSO nor calcitriol exerted any antibacterial activity. In contrast, ST-630 caused a dose-dependent inhibitory activity against *P. acnes.* The antibacterial activity of ST-630 at concentration 12.8 μg was about 2.7-fold lower than that of 15 μg of erythromycin. We conclude that ST-630 (but not calcitriol) exerts a significant inhibitory antibacterial activity towards *P. acnes.*

Example 4

This example sets forth the effects of St-630 and calcitriol on UV-irradiation induced oxidative stress in hairless mouse skin in vivo.

To evaluate whether ST-630 is able to protect skin against oxidative stress in vivo, a separate series of preliminary experiments, the effect of ST-630 on the antioxidant status and biomarkers of oxidative stress of UV-irradiated skin in hairless mice (SKH-1) was studied. In particular, the end-points in the study were: (i) total antioxidant reserves, (ii) different water-soluble antioxidants (vitamin C, GSH, protein sulfhydrls) and lipid-soluble (vitamin E) antioxidants, as well as biomarkers of lipid peroxidation, (iii) the primary procuts of lipid peroxidation (hydroperoxides with conjugated double bonds), and (iv) fluorescent end-products of lipid peroxidation (fluorescent pigments). The measurements were performed on samples of skin of hairless SKH-1 mice after exposure to UV-irradiation (control mice) as well as mice treated with ST-630 either 4 hours before the exposure (pretreated group) or immediately before the exposure (treated group). ST-630 was dissolved in propylene glycol:thanol=80:20 (50 μg/ml) and the solution was applied at a dose of 5 $\mu l/cm^2$ of skin). The UV-source equipped with the cut-off filters (>300 nm) had the output that closely matched the UVA and UVB spectrum of natural sunlight. Total dose applied was 25 $J/cm^2$.

UV-irradiation produced pronounced oxidative stress in skin of SKH-1 mice. This was manifested as a pronounced UV-irradiation induced decrease of all major antioxidants in skin—total antioxidant reserves (about 23%) as well as vitamins C (40%) and E (about 50%), and thiols (about 25%). Simultaneously, we observed slightly elevated levels (by about 15%) of biomarkers of lipid peroxidation in skin. The total dose of UV-irradiation used (25 $J/cm^2$) was similar to that employed by other investigators who observed similar oxidative stress-related changes: a significant depletion of antioxidants and less pronounced accumulation of lipid peroxidation products (Parker, 1994).

Pretreatment of skin with ST-630 caused protection against UV-induced oxidative stress. UV-induced decrease of total antioxidant reserves was essentially eliminated in skin of ST-630 treated animals. Water-soluble antioxidants (vitamin C, GSH and protein sulfhydryls) were also substantially protected in mice pretreated with ST-630. Vitamin E, however, was not protected by ST-630 against UV-induced oxidation (on the contrary, an additional loss of vitamin E was observed in ST-630 pretreated animals). Accumulation of biomarkers of lipid peroxidation (lipid hydroperoxides with conjugated dienes and fluorescent end-products of lipid peroxidation) was reduced in ST-630 pretreated group as well.

Example 5

This example provides methods for determining the effects of ST-630 on keratinocyte proliferation and differentiation Two experimental approaches were performed to assess the effect of ST-630 on the proliferation of cultured human keratinocytes. The first one was the $^3$H-thymidine incorporation experiments that involved the use of a radiolabeled nucleotide which is specifically found in newly synthesized DNA molecules only. The second approach used in this study was the basal cell count. Although it is tedious, the second method is a more definitive way to determine cellular proliferation. Our results clearly establish the potency and the long-lasting effects of ST-630 in inhibiting cellular proliferation as determined by $^{3}$H-thymidine and basal cell count. Overall ST-630 was 10–100 times more potent than calcitriol. The addition of St-630 18 h prior to $^{3}$H-thymidine incorporation caused a dose-dependent inhibition of $^{3}$H-thymidine incorporation into keratinocyte-DNA. ST-630 was approximately 10-fold more active than calcitriol. When the $^{3}$H-thymidine incorporation experiments were performed 42 ha dn 66 h after the initial dosing with $10-^{8}$M of either calcitriol or ST-630, the inhibitory activity of ST-630 was maintained, whereas, the antiproliferative activity of calcitriol diminished with time ST-630 also caused a dose-dependent decreased in the number of basal cells. The analog was 100-fold more active than calcitriol. The inhibition in basal cell count by ST-630 was more pronounced than that of calcitriol when keratinocytes were dosed only for the first 2 days of a 7-day experimental period.

One possible explanation is that the VDR has a higher affinity for ST-630 than for calcitriol land, therefore, it contributed to a greater potency induced by ST-630. However, determination of the binding affinity of the VDR from calf thymus to calcitriol and St-630 indicated that the VDR bound to ST-630 with an approximately 2-fold less affinity than calcitriol. It is also likely that although ST-630 binds to VDR with less affinity as compared to calcitriol, VDR/ST-630 complex may have higher binding affinity for DNA (VDR response element) than VDR/calcitriol complex, which may contribute to its greater biological activity. A third possible explanation is that the prevention of hydroxylation oat C-26 and C-27 positions leads to slower degradation of ST-630 to inactive metabolites and therefore has a much longer half-life in cultured keratinocytes and most likely in the skin in vivo. It has been reported that calcitriol was rapidly metabolized in cultured keratinocytes. In summary, the data indicate that ST-630 is more potent and has a longer-lasting effect than calcitriol in inhibiting keratinocytes proliferation.

Example 6

This example sets forth a process for preparing a topical cream useful for the composition and method of this invention.

| Ingredients: | % w/w |
|---|---|
| Phase A | |
| Purified water | q.s. |
| Glycerin | 3.00 |
| Phase B | |
| Emulsifying wax | 7.5 |
| Propylene glycol dioctanoate | 5.00 |
| Polyolprepolymer | 3.00 |
| Glyceryl stearate (and) PEG-100 stearate | 1.50 |
| Cetyl alcohol | 1.50 |
| Caprylic/Capric triglyceride | 1.00 |
| Caprylic/Capric stearic triglyceride | 1.00 |
| Myristyl lactate | 1.00 |
| Butylated hydroxytoluene | 0.10 |

-continued

| Ingredients: | % w/w |
|---|---|
| Phase C | |
| Propylene glycol | 5.00 |
| ST-630 | 0.01 |
| Phase D | |
| Chorhexidine digluconate | 0.10 |
| Triethanolamine (99%) | q.s. |

Procedure

Dissolve glycerin in water to form Phase A and heat to 70–75° C. Heat ingredients of Phase B with mixing until uniform. Heat Phase B to 70–75° C. With both phases at 70–75° C. add Phase B to Phase with mixing. Continue mixing and cool batch to 40–45° C. Prepare Phase C by adding ST-630 to propylene glycol and mix until dissolved. Add to batch at 40–45° C. and continue mixing. Add Phase D followed by a sufficient amount of triethanolamine such that the resulting pH of the finished cream is 6 to 8. Continue mixing and cool batch to 25–30° C.

Example 7

This example sets forth a process for preparing a topical ointment useful for the composition and method of this invention.

| Ingredients: | % w/w |
|---|---|
| Phase A | |
| Purified water | 16.39 |
| Tetrasodium EDTA | 0.05 |
| Phase B | |
| White petrolatum | 70.00 |
| Mineral oil NF | 5.00 |
| Steareth-2 | 4.00 |
| Microcrystalline was | 0.50 |
| Butylated hydroxy6toluene | 0.05 |
| Phase C | |
| Propylene glycol | 4.00 |
| ST-630 | 0.01 |

Heat the purified water in Phase A to 75° C., dissolve the sodium EDTA and maintain temperature. Hear the ingredients in Phase B to 75–80° C. and mix until uniform. Dissolve ST-630 in propylene glycol and add to Phase B, mix until uniform and maintain temperature. Add Phase A to Phase B under mixing. Continue mixing and cool to room temperature.

Example 8

This example sets forth a process for preparing a gel useful for the composition and method of this invention.

| Ingredients: | % w/w |
|---|---|
| Ethanol | 90.09 |
| Propylene glycol | 5.00 |
| Polyolprepolymer-2 | 3.00 |
| Hydroxypropyl cellulose | 1.80 |

-continued

| Ingredients: | % w/w |
|---|---|
| Butylated hydroxytoluene | 0.10 |
| ST-630 | 0.01 |

Disperse the hydroxypropyl cellulose in part or the ethanol and mix until hydrated to form a clear smooth gel. Mix the rest of the ethanol and propylene glycol until uniform. Add polyolprepolymer-2 to the mixture and mix until dissolved. Add ST-630 and mix until dissolved. Add this mixture to ethanol HPC gel and mix until uniform. Emollients such as glycerin may be included in the formula, replacing the equivalent amount of ethanol.

EXAMPLE 9

This example sets forth a process for preparing a solution or liquid useful for the composition and method of this invention. Ingredients:

| Ingredients: | % w/w |
|---|---|
| Ethanol | 91.69 |
| Propylene glycol | 5.00 |
| Polyolprepolymer-2 | 3.00 |
| Hydroxypropyl cellulose | 0.20 |
| Butylated hydroxytoluene | 0.10 |
| ST-630 | 0.01 |

Mix ethanol and propylene glycol until uniform. Dissolve the poplyolprepolymer-2 in the mixture followed by BHT. Add ST-630 and mix until dissolved. Film forming agents such as povidone may also be added if desired. Also, emollients such as glycerin and other solvents such as polyethylene glycol 400 may be included in the formula, replacing the equivalent amount of ethanol.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

The subject matter claimed is:

1. A method for reducing the rate at which skin of a human ages, which method comprises topically administering the compound 26, 27-hexafluoro-1,25-dihydroxy vitamin $D_3$ to the skin of the human in need thereof on a daily basis in an antioxidative amount for a time sufficient to reduce the rate of skin aging.

2. The method of claim 1, wherein the compound is administered by topically administering a topical, pharmaceutically-acceptable excipient in combination with the compound.

3. The method of claim 2, wherein the topical composition is an ointment comprising about 0.0001% weight to about 0.01% weight of the compound.

* * * * *